(12) United States Patent
Lawrence et al.

(10) Patent No.: US 7,796,241 B2
(45) Date of Patent: Sep. 14, 2010

(54) EGG MICRO-CRACK DETECTION SYSTEMS

(75) Inventors: Kurt C. Lawrence, Watkinsville, MD (US); Seung C. Yoon, Athens, GA (US); Gerald W. Heitschmidt, Athens, GA (US); Deana Jones, Athens, GA (US); Bosoon Park, Bogart, GA (US); Vernon A. Savage, Watkinsville, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/231,785

(22) Filed: Sep. 5, 2008

(65) Prior Publication Data
US 2009/0091744 A1   Apr. 9, 2009

Related U.S. Application Data

(60) Provisional application No. 60/970,759, filed on Sep. 7, 2007.

(51) Int. Cl.
*A01K 43/00* (2006.01)
*G01N 33/08* (2006.01)
*G06K 9/00* (2006.01)

(52) U.S. Cl. .............................. 356/53; 356/64; 356/65; 356/66; 356/67; 382/110

(58) Field of Classification Search ....................... None
See application file for complete search history.

(56) References Cited

U.S. PATENT DOCUMENTS

| 2,842,263 | A | * | 7/1959 | Giraudet ...................... 206/485 |
| 3,106,234 | A | * | 10/1963 | Conrad .......................... 99/495 |
| 3,314,804 | A | * | 4/1967 | Kosikowski ................. 53/405 |
| 5,017,003 | A | * | 5/1991 | Keromnes et al. ............. 356/53 |
| 5,082,366 | A | * | 1/1992 | Tyson et al. ................ 356/35.5 |
| 5,598,807 | A | * | 2/1997 | Cox et al. .................... 119/6.8 |
| 5,615,777 | A | | 4/1997 | Weichman et al. |
| 5,898,488 | A | * | 4/1999 | Kuhl ........................... 356/53 |
| 6,323,943 | B1 | * | 11/2001 | Maruyama et al. ......... 356/28.5 |
| 6,800,315 | B2 | * | 10/2004 | Yousef et al. ............... 426/248 |
| 2004/0149497 | A1 | * | 8/2004 | Larsen et al. ............... 177/229 |
| 2009/0277199 | A1 | * | 11/2009 | Manas et al. .................. 62/129 |

FOREIGN PATENT DOCUMENTS

WO    WO 2006062491 A2 * 6/2006

OTHER PUBLICATIONS

De Ketelaere, B. et al., "Non-destructive Measurements of the Egg Quality", *World's Poultry Science Journal*, vol. 60, 2001, pp. 289-302.
Lin, J., et al., "Effects of Temperature and Washing on the Strength of Eggs," *Presentation at American Society of Agricultural Engineers*, 1999, Paper No. 99-6071.

* cited by examiner

*Primary Examiner*—Tarifur Chowdhury
*Assistant Examiner*—Gordon J Stock, Jr.
(74) *Attorney, Agent, or Firm*—Gail E. Poulos; John D. Fado

(57) ABSTRACT

An avian eggshell egg-check/crack detection system was developed to aide official egg graders. It includes an imaging system and a device to produce negative pressure in an egg chamber.

10 Claims, 13 Drawing Sheets

Fig. 11A-D

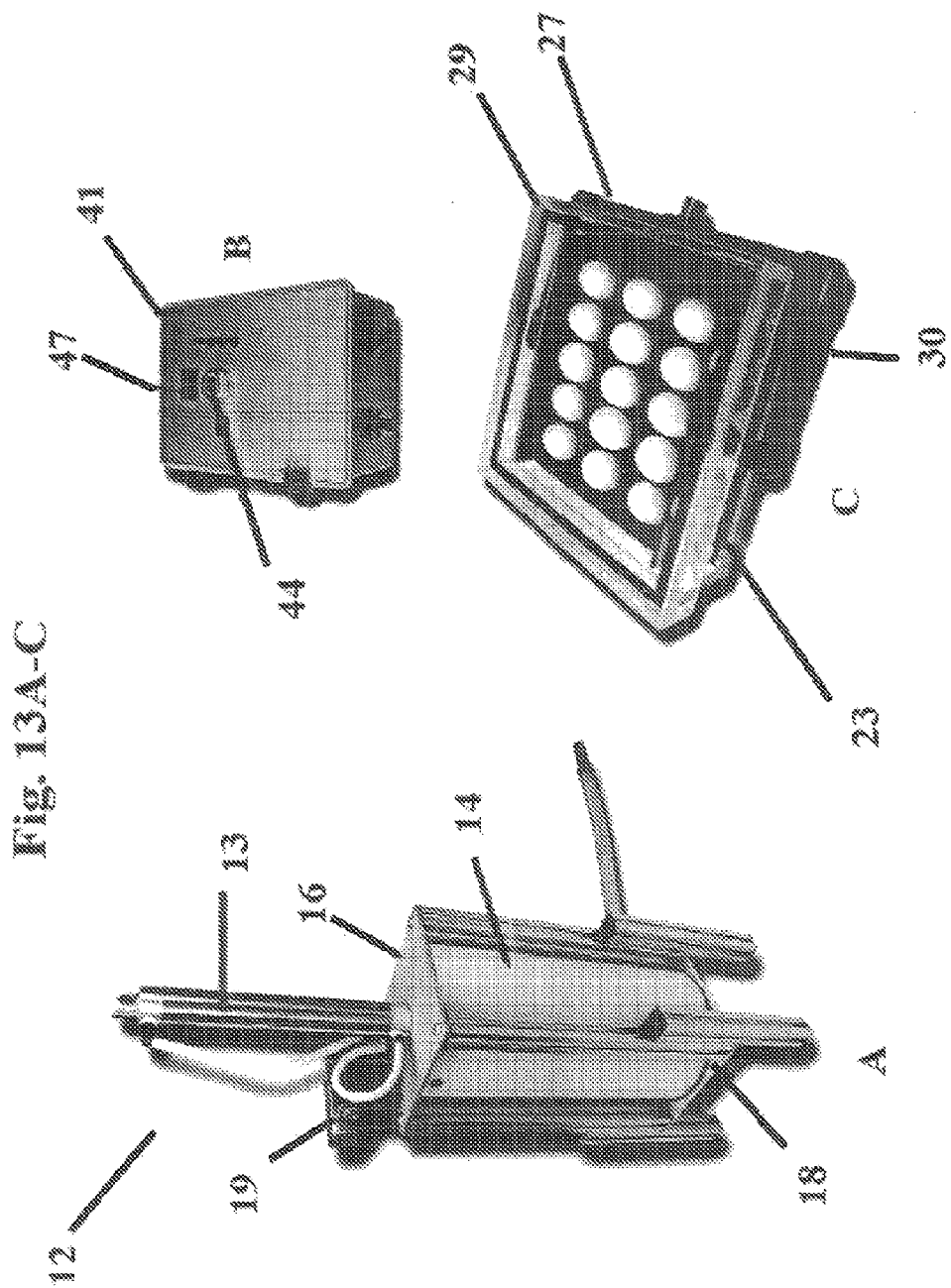
Fig. 13A-C

EGG MICRO-CRACK DETECTION SYSTEMS

This application is a non-provisional application claiming benefit of provisional application 60/970,759 filed Sep. 7, 2007; which is herein incorporated by reference in its entirety.

BACKGROUND OF THE INVENTION

1. Field of the Invention

This invention relates to avian egg micro-crack detection systems and to methods for using the systems.

2. Description of the Related Art

The contents of an avian egg are enclosed with two shell membranes and a shell. An eggshell check is defined as an opening in the eggshell with the shell membranes intact and no egg contents voided. A crack is an opening in an eggshell where the membranes are compromised and egg contents are voiding through the opening. To detect checks and/or cracks in shell eggs during processing, the egg industry uses high-speed acoustic systems. Once the eggs are processed and the desired percentage of checked or crack eggs are removed, the remaining eggs are boxed for sale. Prior to shipment, human graders sample a grading lot of eggs (currently 100) to ensure that the high-speed systems are operating within specifications for a given grade of egg, such as, Grade A Large Eggs. Currently these human graders use a longstanding technique of visually candling and audibly "belling" an egg to detect defects such as checks or cracks. Belling an egg is a technique that includes gently tapping two eggs together and listening for a dull sound. The dull sound is an indication of a check or crack. Once heard, the grader then visually confirms there is a disruption in the shell. In some of the high-speed sorting and grading systems, very small egg cracks, known as micro-cracks, can occur and initially go undetected by the human graders. Although a large number of automatic inspection devices have been proposed, candling of eggs in a direct light source is still used by human inspectors to validate the grade of a lot. When the number of eggs processed in a graded facility is large, there is a need to increase the number of inspectors. Moreover, there is an upper limit to the accuracy and speed at which the inspectors can operate because of the concentration required. Fatigue is a major limiting factor.

Various automated systems have been used to detect checks and cracks and include tapping of eggs so that a check or crack can be recognized from the type of sound which develops from the tapping, (see for example, Canadian Patent No. 927,965 issued Jun. 5, 1973 to Bliss). Alternatively the change in elastic characteristics can be noted by tapping with a small hammer, which recoils less from places, which are cracked, (see for example Dutch Patent Application No. 286, 485). If an egg is vibrated, a damping of the vibration on the cracked places can be detected.

Examples of previous patents or patent applications which have attempted to solve the problems are as follows:

East German Application No. 293,340, published Aug. 29, 1991 discloses utilizing the intensity of light transmitted through eggs as a criterion to distinguish between flawed and perfect eggs.

European Patent Application No. 373,261, published Jun. 20, 1990, discloses locating the eggs on a conveyor roller track at high speed while examining them by a detector. Flawed eggs are discharged from the conveyor at an appropriate position downstream of the inspection station.

Dutch Patent Application No. 8,303,804, published Jun. 3, 1985 provides a system for alleviating operator eyestrain.

U.S. Pat. No. 4,487,321, issued Dec. 11, 1984 to Bliss, utilizes an elongated pointer for movement into and out of engagement with eggs. Signal generators respond to pointer movement for generating signals for identifying the position of selected articles when they are engaged by the pointer.

U.S. Pat. No. 4,182,571 issued Jan. 8, 1980 to Furuta et al., utilizes light reflection signals obtained from light beams passed through an egg to select eggs containing blood.

U.S. Pat. No. 4,161,366 to Bol et al. and issued Jul. 17, 1979, utilizes a laser as a light source to scan the egg. The intensity of light penetrating into the egg is measured. Part of the light penetrating into the egg is diffusely reflected and part is absorbed while entering the shell, particularly in the case of brown eggshells. The light that penetrates inside the egg is strongly scattered by the shell structures. This scattered light is dissipated by multiple reflections of the inner surface of the shell and the yoke sac. The egg glows uniformly. The light radiating from the egg corresponds to the structure of the shell. In particular, the egg shines more brightly when the scanning light beam falls on thin, glassy spots of the shell or cracks. In some instances, an actual flash of light may even be observed.

The process and system of the invention of U.S. Pat. No. 4,161,366 generates a characteristic flash of light for cracks, pinholes and regions of thin shell caused by cage marks or body checks. Some of these flaws may be acceptable but a flaw characterized by an actual disruption of the shell integrity never is acceptable. It is therefore, important to distinguish between checks and cracks and other shell-related flaws.

U.S. Pat. No. 5,615,777 (Apr. 1, 1997) discloses an egg candling system which scans the surface of an egg for flaws such as pin holes, cracks, thinned shell regions, etc. using a laser beam. The light beam is vibrated with a rocking/rotating movement to describe a closed curve such as a circle, ellipse, or an ellipse so narrow that it is effectively a straight line. The utilization of such a light beam allows identification of flaws due to the character of the progression of light emanating from the egg. The patent further discloses an apparatus for rotating the egg about its longitudinal axis in the path of the beam or beams. The apparatus also includes apparatus for forming the vibrating beam such as mirrors vibrated by out of phase electro-magnetic vibration or piezo-electric actuators.

Lin et al. (ASAE Paper No. 99-6071, Jul. 18-22, 1999, Toronto, Ontario, Canada) disclose a non-destructive method for measuring eggshell strength using loading and unloading of hydrostatic pressure on eggs. One aspect of the disclosure was to determine the loading pressure needed to extend cracks on the eggshell. They found that when the hydrostatic pressure was suddenly removed from the tested egg, the micro-crack would extend. Their preliminary results showed that a smaller pressure drop from loading to unloading could make egg checks and cracks more visible.

De Ketelaere et al., (World's Poultry Science Journal, Volume 60, 289-302. September 2004) reports the use of impactor technology for eggshell crack detection. One device uses a small impactor to excite the eggshell. The amplitudes of the rebounds are measured to determine eggshell integrity. The reference then reports another impactor method where an egg is rolled over a series of small metal objects under which a piezo-sensor is mounted. It is alleged that this measuring principle reveals only local shell quality information and the crack detectors have to test several locations for each egg in order to obtain satisfactory results. In another approach, the response of the egg itself to the impactor is considered by looking at the number of resonant peaks.

While various systems have been developed for detecting checks and cracks in eggshells, there still remains a need in the art for a more effective system for detecting cracks and checks, especially micro-cracks to assist graders in validating the grade of an egg. The present invention, different from prior art systems, provides a system which uses negative pressure and an imaging system to enhance crack detection.

SUMMARY OF THE INVENTION

It is therefore an object of the present invention to provide a system for detecting cracks and/or checks in avian eggs using negative pressure, a lighting system, and an imaging system.

Another object of the present invention is to provide a system for detecting cracks and/or checks in at least one avian egg wherein said system includes a vacuum system and a lighting system.

A still further object of the present invention is to provide a system for detecting cracks and/or checks in at least one avian egg wherein said vacuum system includes a vacuum pump, a control unit, and a vacuum egg chamber.

A still further object of the present invention is to provide a system for detecting cracks and/or checks in at least one avian egg wherein said control unit includes a push button switch, a control circuit, and an air solenoid valve.

Another object of the present invention is to provide a system for detecting cracks and/or checks in at least one avian egg wherein said vacuum egg chamber includes a light system and a vacuum box.

A still further object of the present invention is to provide a system for detecting cracks and/or checks in at least one avian egg wherein said light system includes lights, a light-positioning plate, constant current drivers, potentiometers, light guides, an aperture plate, and a DC power supply.

A still further object of the present invention is to provide a system for detecting cracks and/or checks in at least one avian egg wherein said vacuum box includes egg rollers, lights guides and a chamber lid.

Another object of the present invention includes providing a system for detecting cracks and/or checks in at least one avian egg including a vacuum system, a lighting system, and an imaging system.

A still further object of the present invention is to provide a system for detecting cracks and/or checks in at least one avian egg wherein said imaging system includes at least one camera, a computer, a pressure control enclosure, and optionally an oscilloscope.

Another object of the present invention is to provide a method for detecting checks and/or cracks in at least one avian egg that includes the steps of placing a egg into a vacuum egg chamber, illuminating said at least one avian egg, creating a negative pressure vacuum in said vacuum egg chamber, and determining the presence of a crack and/or a check in said at least one avian egg.

A still further object of the present invention is to provide a method for detecting checks and/or cracks in at least one avian egg wherein said step of creating a negative pressure vacuum is achieved using a vacuum system that includes at least a vacuum pump and a control box.

A still further object of the present invention is to provide a method for detecting checks and/or cracks in at least one avian egg wherein said control box includes a push button switch and a solenoid valve.

A still further object of the present invention is to provide a method for detecting checks and/or cracks in at least one avian egg wherein said vacuum egg chamber includes egg rollers, light guides, and a chamber lid.

A still further object of the present invention is to provide a method for detecting checks and/or cracks in at least one avian egg wherein said step of illuminating is achieved with a lighting system that includes lights, a light-positioning plate, light guides, and an aperture plate.

Another object of the present invention is to provide a method for detecting checks and/or cracks in at least one avian egg that includes the steps of placing at least one avian egg in a vacuum egg chamber, creating a negative pressure vacuum in said egg chamber, illuminating said at least one egg with a lighting system and determining the presence of a crack and/or check in said egg using an imaging system.

A still further object of the present invention is to provide a method for detecting checks and/or cracks in at least one avian egg wherein said imaging system includes at least one camera, a computer, and a pressure control block.

Further objects and advantages of the invention will become apparent from the following description.

BRIEF DESCRIPTION OF THE DRAWINGS

FIG. 11A shows an image of an egg taken at atmospheric pressure. FIG. 11B shows an image of an egg taken at negative pressure. FIG. 11C shows an image of an egg where image B was divided by image A. FIG. 11D shows an image of an egg after simple threshold and segmentation image processing.

FIGS. 13A-13C are photographs of the parts of an embodiment of system 10 without imaging system 40. FIG. 13A shows vacuum pump 12 including double ended cylinder 13, six-inch PVC cylinder 14, gasket sealed aluminum top 16, gasket sealed aluminum bottom 18, and solenoid valve 19. FIG. 13B shows control enclosure 41, push button switch 44, and pressure control block 47. FIG. 13C shows vacuum egg chamber 23 including egg rollers 27, chamber lid 29, and PVC pipes 30.

DETAILED DESCRIPTION OF THE INVENTION

Figure 1:
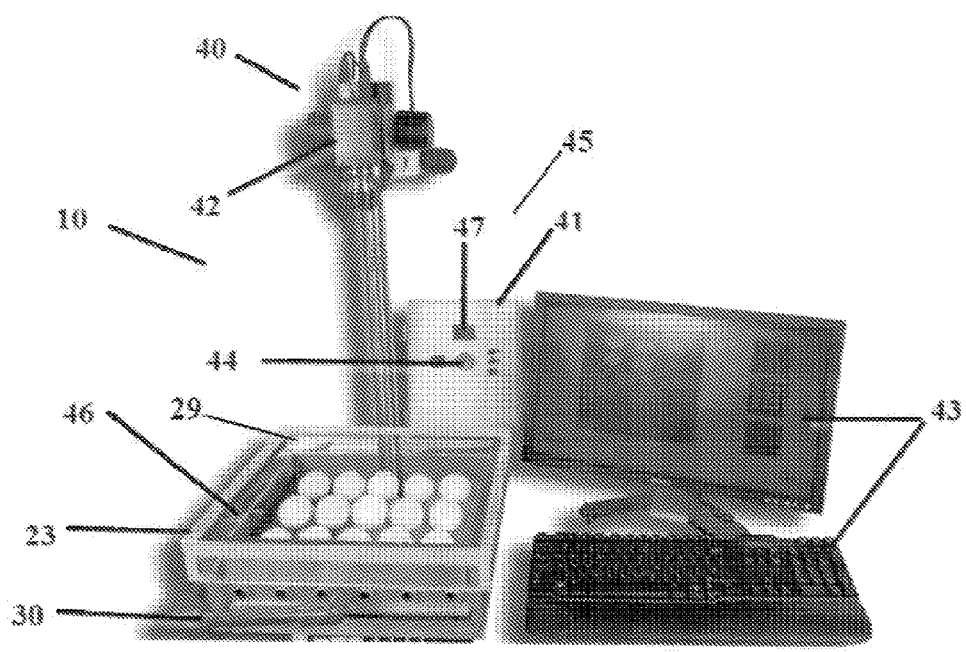
FIG. 1 is a photograph of detection system 10 showing imaging system 40 including camera 42 and computer 43, control box 41 including push button switch 44 and pressure control block 47; vacuum egg chamber 23, chamber lid 29, pressure sensor 46, and PVC pipes 30.

The present invention is a system for detecting cracks, especially micro-cracks and checks in avian eggshells using negative air pressure and an image system 40 (FIG. 1). System 10 of the present invention includes a vacuum system, a lighting system, and image system 40.

Figure 2:
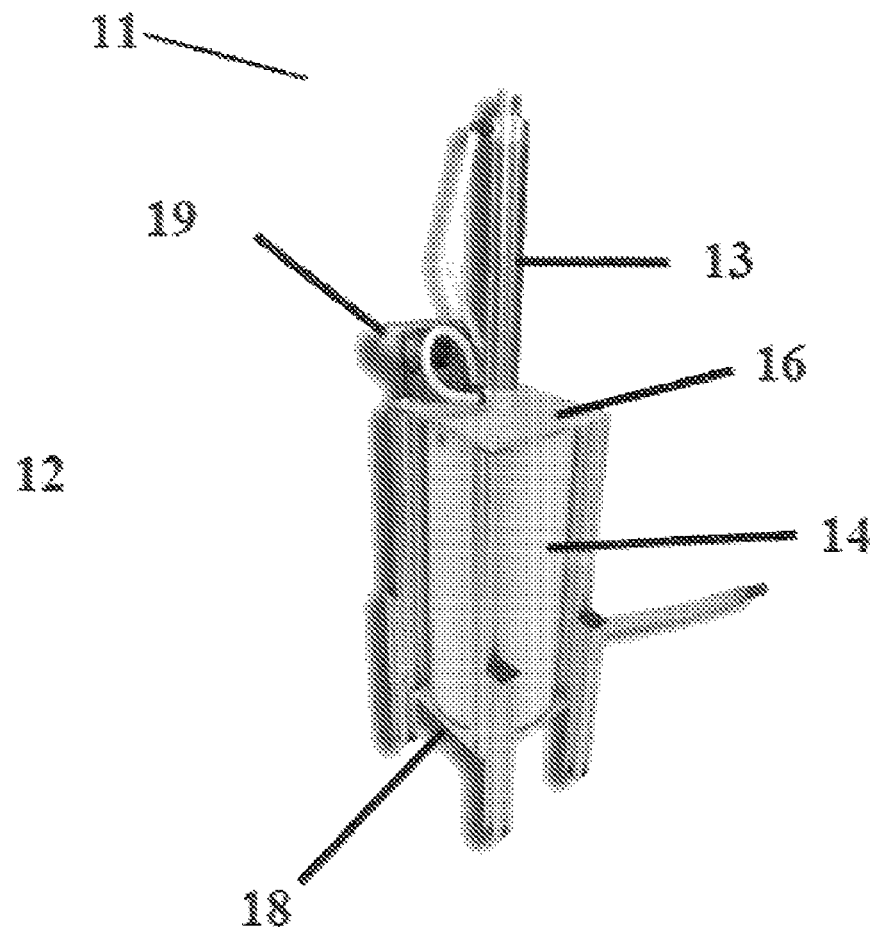
FIG. 2 is a photograph of vacuum pump 12 including double ended air cylinder 13, six-inch PVC cylinder 14, gasket sealed aluminum top 16, gasket sealed aluminum bottom 18, and solenoid valve 19.
Figure 3:
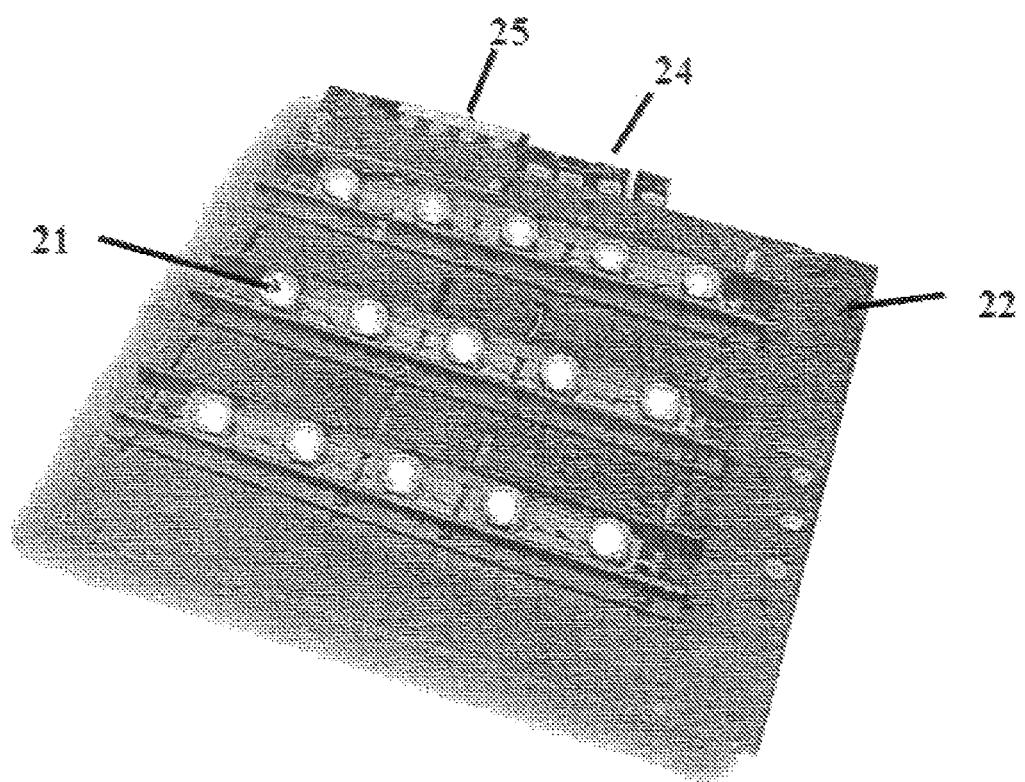
FIG. 3 is a photograph of a part of light system showing light-positioning plate 22, lights 21, constant current drivers 24, and potentiometers 25.
Figure 4:
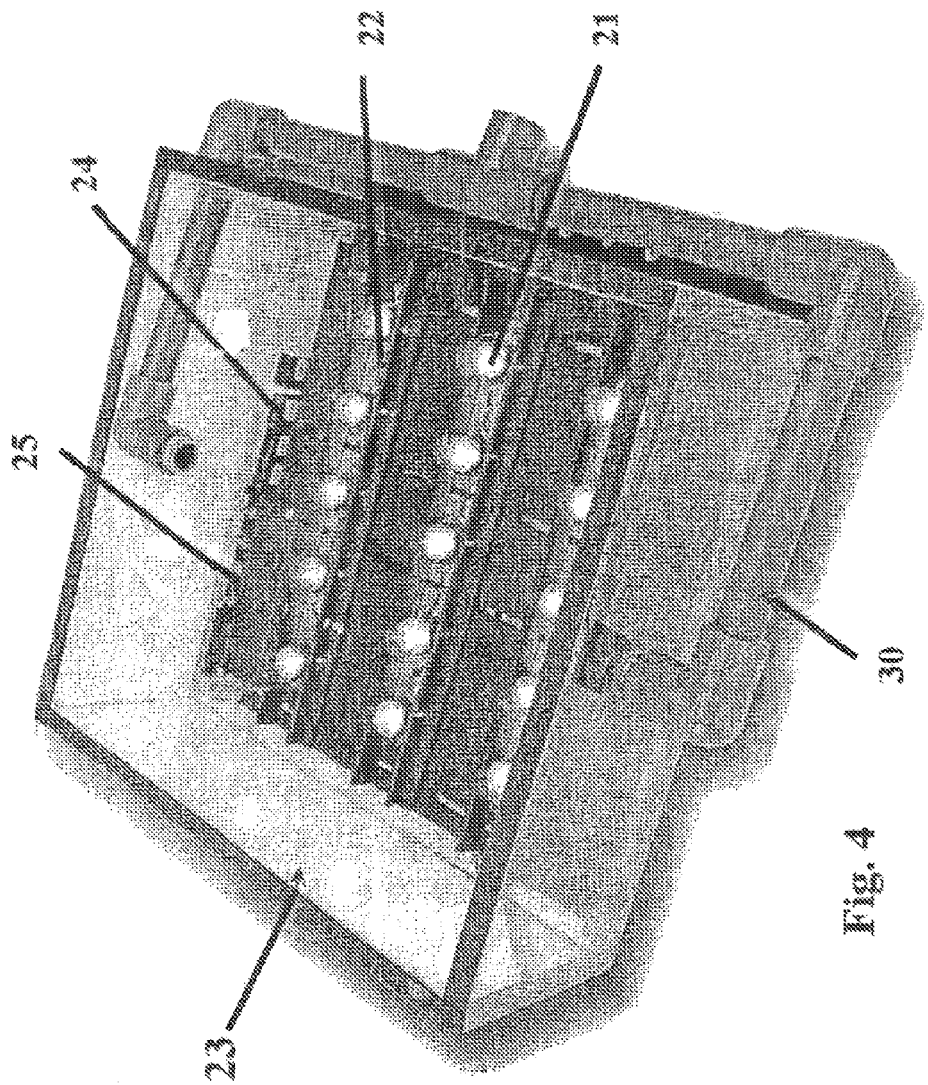
FIG. 4 is a photograph of part of lighting system and part of the vacuum egg chamber 23 including light-positioning plate 22, lights 21, constant current drivers 24, potentiometers 25, and PVC pipes 30.
Figure 5:
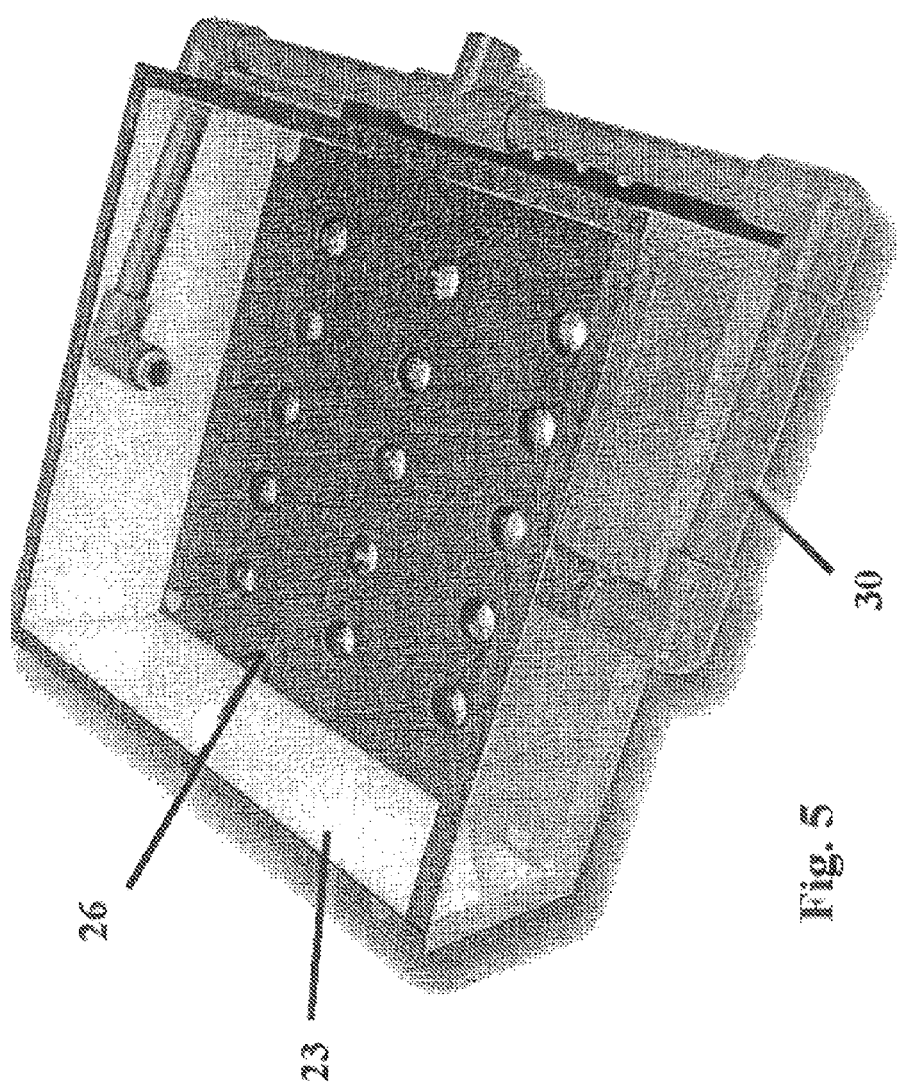
FIG. 5 is a photograph of vacuum egg chamber 23 showing light-aperture plate 26 and PVC pipes 30.
Figure 6:
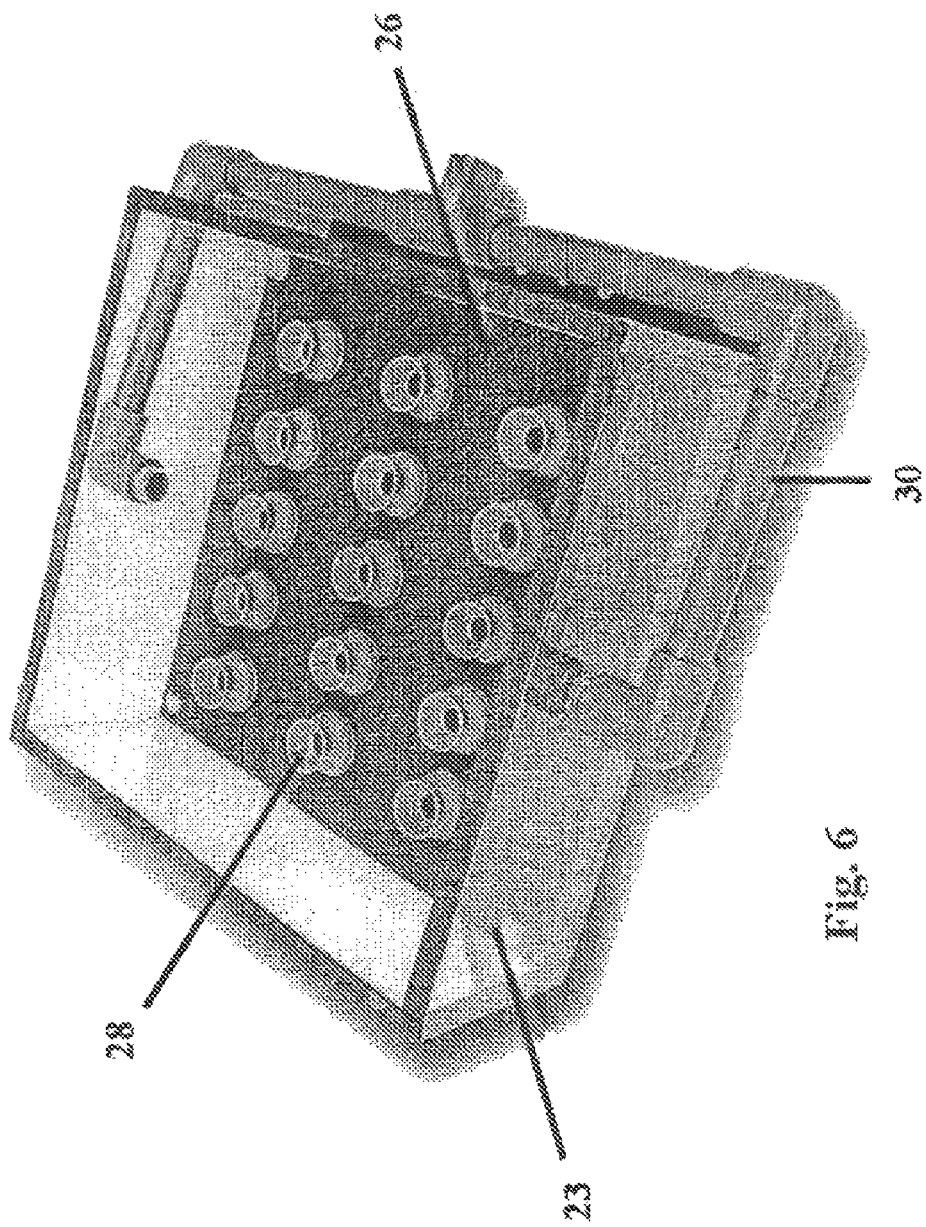
FIG. 6 is a photograph of vacuum egg chamber 23 showing light-aperture plate 26, light guides 28, and PVC pipes 30.
Figure 7:
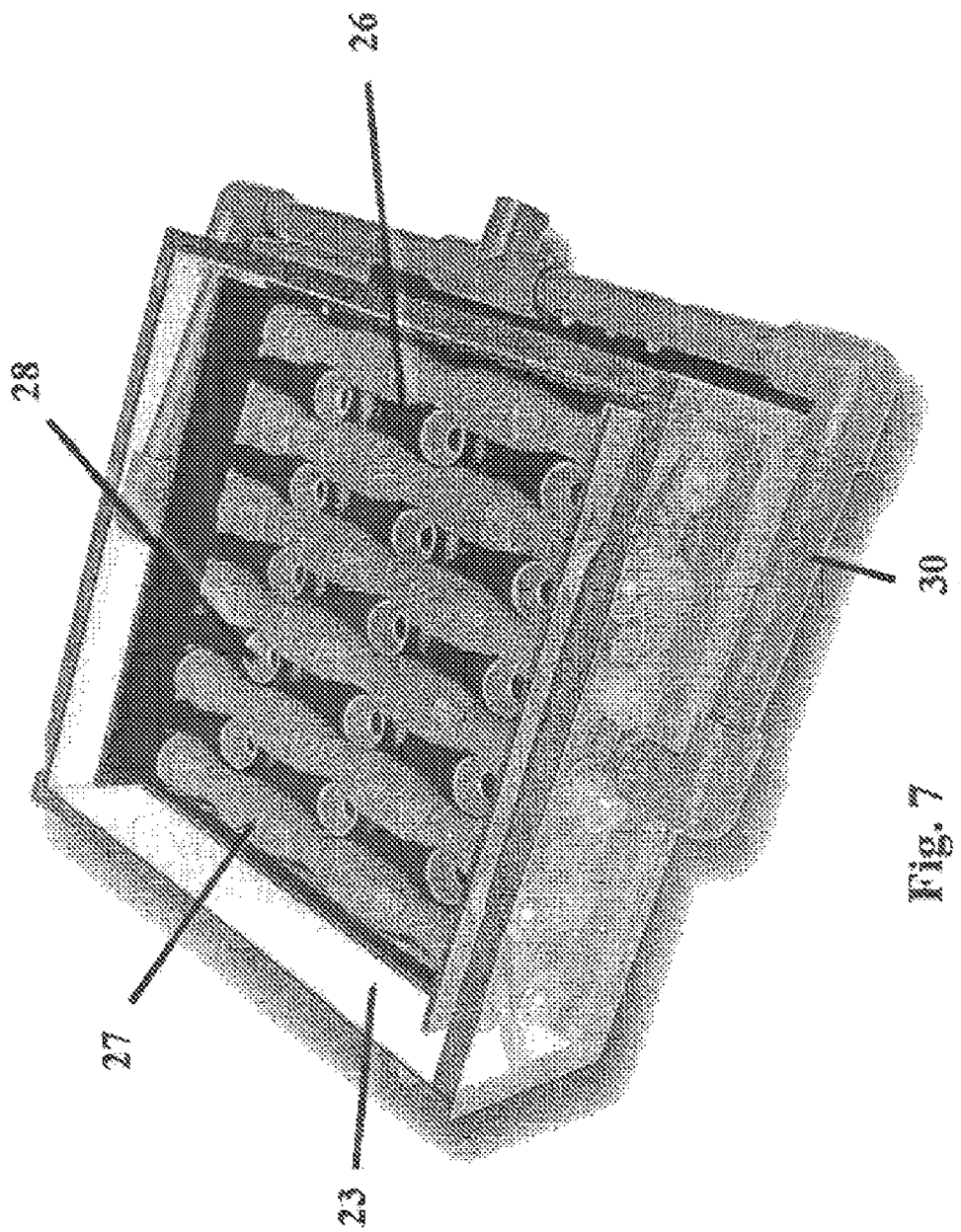
FIG. 7 is a photograph of vacuum egg chamber 23 showing light-aperture plate 26, egg rollers 27, light guides 28, and PVC pipes 30.
Figure 8:
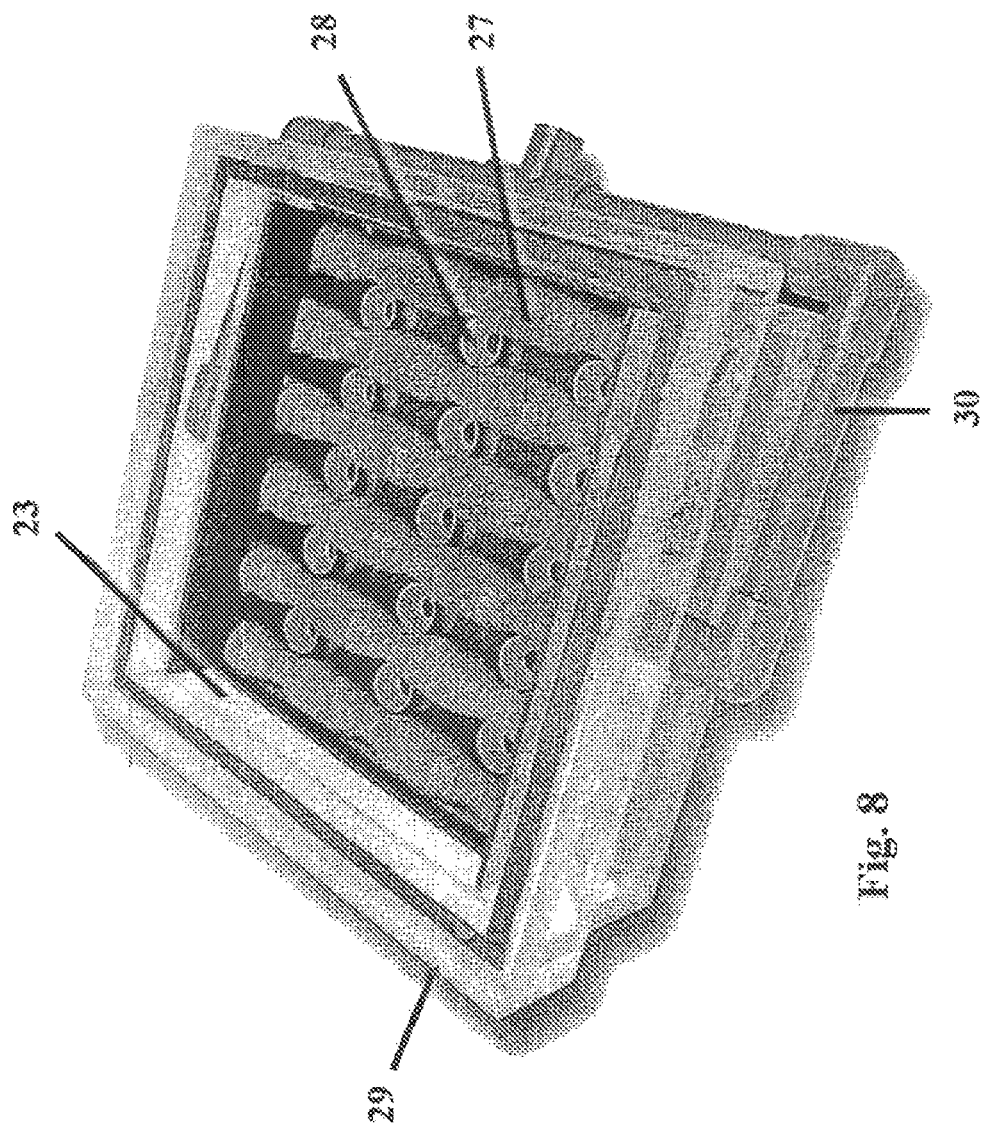
FIG. 8 is a photograph of vacuum egg chamber 23 showing egg rollers 27, light guides 28, chamber lid 29, and PVC pipes 30.
Figure 9:
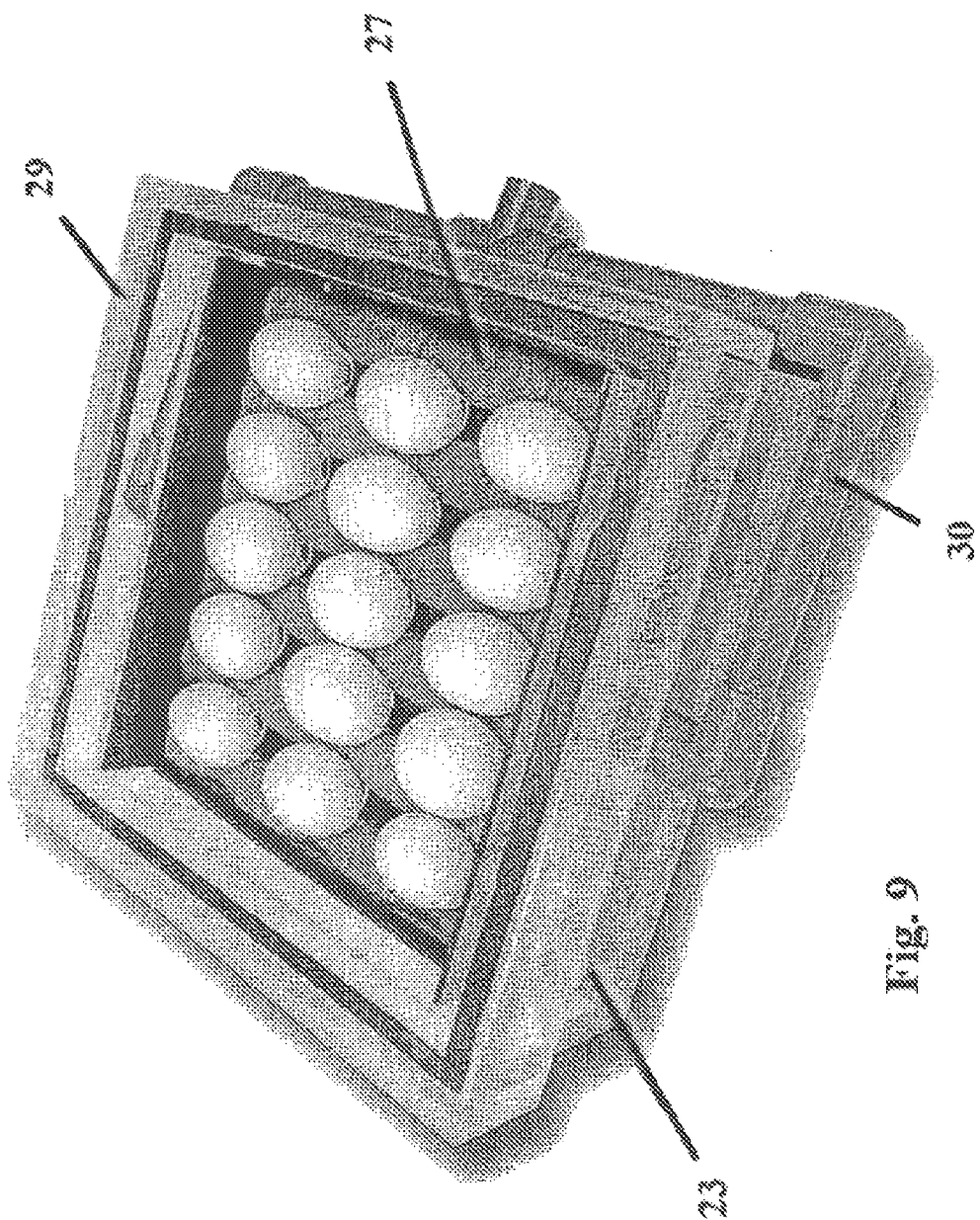
FIG. 9 is a photograph of egg chamber 23 showing eggs on egg rollers 27, chamber lid 29, and PVC pipes 30.

The vacuum system includes vacuum pump 12, push button switch 44, control enclosure 41, control unit (FIG. 10), solenoid valve 19, vacuum chamber 23, chamber lid 29, egg rollers 27, and PVC pipes 30 (FIGS. 1 and 2). Vacuum pump 12 is driven by compressed air of about 100 pounds per square inch (psi) (FIG. 2). Vacuum 12 is connected to a double ended air cylinder 13 having about a 3.8 cm (about 1.5 inch) bore and about a 20.3 cm (about 8 inch) stroke (Model MRS-178-DXPK, Bimba Manufacturing Co., Monee, Ill.). Air cylinder 13 is attached to a plunger (not shown) which is used to rapidly create a vacuum, working like a large syringe, in egg chamber 23 with chamber lid 29 (FIG. 1). Vacuum pump 12 has an approximately six-inch diameter PVC cylinder 14 for the outside walls and has gasket-sealed aluminum top 16 and bottom 18 plates. The plunger seal (not shown) is made with about a six inch diameter NuLine Fab/Buna U-cup fabric and nitrile piston cup. One of ordinary skill in the art could modify the plunger seal to include other commercial vacuum seals such as a Honeywell diaphragm assembly model 312809C. The seal is attached by a rod to the ram of the two-way air cylinder 13. The two-way air cylinder 13 is controlled by a standard 4-way solenoid valve 19 (AAA Products International, Dallas, Tex.). One input of the 4-way solenoid valve 19 is connected to about 100 psi of compressed air and the other input is left open to the atmosphere. The outputs of the valve are connected to each end of the double-ended air cylinder 13. To create a vacuum, solenoid valve 19 is energized which rapidly contracts the ram of the double-ended air cylinder 13 and pulls the plunger up in PVC cylinder 14 causing a vacuum to be generated in the bottom portion of PVC cylinder 14. Once the desired vacuum is reached of about 9 inches Hg, as determined by the control circuit, the solenoid valve 19 switches back to its original state and the ram extends again, sending the plunger back to the bottom of cylinder 14 and forcing air back into chamber 23 with lid 29, returning chamber 23 with lid 29 to atmospheric pressure. Vacuum pump 12 connects to chamber 23 with standard ¾ inch flexible vacuum tubing connected to the bottom of cylinder 14. One cycle of the vacuum system, from atmospheric pressure to minimum negative pressure and back to atmospheric pressure, takes about 500 ms. One of ordinary skill in the art could modify the vacuum system to include a commercial vacuum pump such as, for example, a Venturi-type vacuum generator. A vacuum pump that can quickly draw a vacuum in the appropriately-sized chamber 23 with lid 29 should be used since the egg crack or check opens because of the rapid change in negative pressure. Egg chamber 23 is constructed to hold any number of eggs. For description purposes, a 15-egg chamber is exemplified. One of ordinary skill in the art at the time the claimed invention was made could readily modify the chamber to hold any number of eggs based on the forgoing description. For a 15-egg chamber 23, about a 1.27 cm thick Acrylite® abrasion-resistant acrylic sheeting is used for the sides of chamber 23. About a 1.9 cm acrylic sheeting is used for the chamber lid 29 and bottom of chamber 23. Chamber 23 has inside dimensions of approximately 30.48 cm length×approximately 30.48 cm width×approximately 10.16 cm height for a 15-egg chamber. In chamber 23, eggs are placed on six standard commercially available egg rollers (Sanova Engineering USA, Elk Grove, Ill.) 27 resulting in three columns with five eggs each. Chamber lid 29 (FIG. 1) is rigid to prevent flexing which can distort images captured by camera 42. Attached to the sides of chamber 23, are two PVC ¾ inch pipes 30 which are connected together and attached to the vacuum pump 12 with flexible tubing. Egg rollers 27 are connected to each other such that the eggs can all be simultaneously turned for additional imaging. Vacuum chamber 23 has a seal (not shown) and an external handle (not shown) to manually turn rollers in between sets of images (atmospheric images and negative pressure images). Alternatively rollers 27 can be motorized and controlled by circuit and software. Once a set of images is taken, a programmable stepper motor could be used to turn rollers 27 a fixed angular rotation. Then a second set of images is collected and the stepper motor could be signaled to rotate again. This process would then be repeated until the egg is rotated at least about 360 degrees.

The lighting system includes lights 21, light-positioning plate 22, constant current drivers 24, potentiometers 25, light-aperture plate 26, and light guides 28 (FIGS. 3-8). For lighting, several options are available. Traditional incandescent lights, quartz-tungsten halogen lamps, or other broad spectrum lights can be used in the lighting system. Narrow spectrum LED lights and a laser can also be used. However, these examples may not be ideal for large numbers of eggs. Since each egg radiates incident light, the light intensity should be lower for the center eggs in a group and brighter for eggs near the edges of chamber 23. Individual high-power white light emitting diodes (LEDs), positioned below each egg, are preferred so that the light intensity into each egg can be adjusted if needed. In practice, LEDs are grouped together based on location, to provide more uniform lighting for the entire set of eggs. Once adjusted, the light intensities are fixed. Alternately, a lighting feedback control loop can be used such that the illumination of each egg can be adjusted for every set of eggs based on the results of a preliminary capture image. This can be accomplished by taking an illumination image at atmospheric pressure with digital camera 42 and using software to calculate the mean intensity of each egg. Then a lighting control circuit will be used to adjust the intensity of each light. Repeated images can then be used to check intensities until the mean intensity of every egg is approximately the same. In practice, for a 15-egg chamber, 15 white Luxeon® I STAR/O LED lights 21 (Phillips Lumileds Lighting Company, San Jose, Calif.) provide the necessary illumination and are powered by a standard DC power supply (not shown) which can be housed in control enclosure 41. Lights 21 are mounted on a light-positioning plate 22 painted flat-black to reduce reflections. For a 15 egg chamber, plate 22 is approximately 33×38 cm (13×15 inches). One of ordinary skill in the art could readily determine the size of plate 22 based on the number of lights 21 positioned under each egg. Lights 21 are mounted outside and under chamber 23 to reduce the potential for any severely broken eggs leaking onto lights 21. Plate 22 serves to position LEDs 21 and acts as a heat-sink. To provide variable illumination, the LEDs 21 are wired according to position and controlled with four constant current drivers 24 with potentiometers 25 (FIGS. 3 and 4) (BuckPuck 3021-D-E-350, LEDDynamics, Randolf, Vt.) as shown below for illuminating 15 eggs:

A D D D A
B C C C B
A D D D A

For a 15-egg system, LEDs are controlled by four potentiometers 25 in four groups: potentiometer A controls the four corner LEDs, potentiometer B controls the two middle end LEDs, potentiometer C controls the 3 inside LEDs, and potentiometer D controls the 6 middle side LEDs. One of ordinary skill in the art could determine the grouping of LEDs for uniform illumination of all eggs for different numbers and configurations of eggs. On the inside bottom of chamber 23, a thin light-aperture plate 26 with the same number of holes as eggs and light guides 28 is inserted. Light guides 28 can be cut vacuum-loader cups. One of ordinary skill in the art could readily determine how to make guides 28 using, for example, rigid plastic tubing. One of ordinary skill in the art could also adjust the diameters of the holes in the light-aperture plate to vary the illumination intensity for various egg locations. Chamber 23 is mounted on top of LED lights 21 to ensure alignment between lights 21, rollers 27, eggs, and camera 42 (FIGS. 1 and 5-9). One of ordinary skill in the art could readily use chambers of different sizes. A chamber large enough to mount camera 42 inside chamber 23 could be constructed. This type of chamber has the advantage of not having to be transparent, except for openings for lights and an observation port for use by the grader. This would eliminate the potential distortion between the atmospheric image and the negative pressure image. A chamber of this size would likely require a larger vacuum pump 12 because of its anticipated larger volume.

Figure 10:
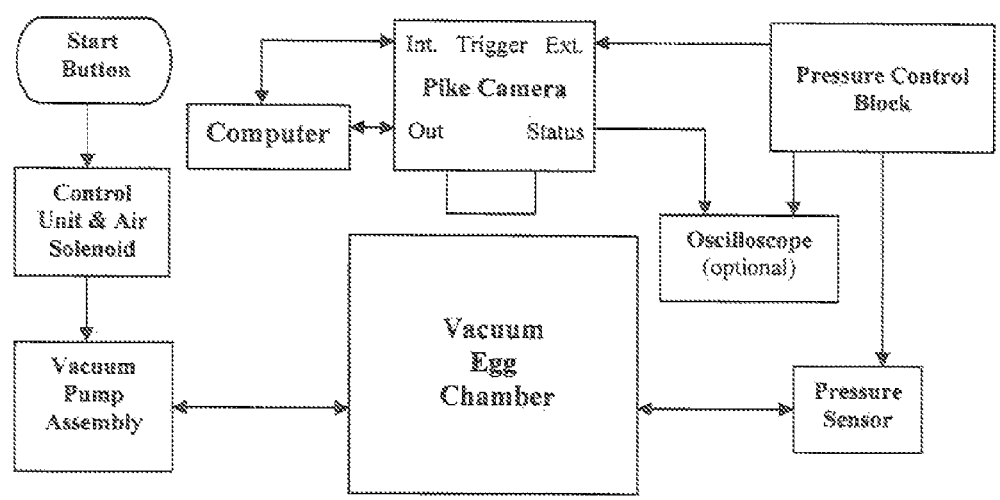
FIG. 10 is a drawing of the control circuit.

Image system 40 consists of at least one camera 42, computer 43, software (not shown) digital pressure sensor 46, pressure control block 47, and optional digital oscilloscope (FIG. 10). Camera 42 is a high resolution digital camera (Pike 421-B, Allied Vision Technologies, Newburyport, Mass. (FIG. 1)). Other digital cameras can be used, provided the camera's resolution is sufficient to detect even the smallest checks or cracks. Resolution is a function of the number of pixels in the camera, the lens, and the working distance. For a 15-egg system 10, an approximately 2000 pixel by 2000 pixel imaging system 40 with a 28 mm focal length lens (Xenoplan 2.0/28 mm Compact Style, Schneider Optics, Hauppauge, N.Y.) and about a 40 cm working distance has sufficient resolution to detect the small micro-cracks. Optionally, a long-pass filter (Type 040 Yellow-Orange, Schneider Optics, Hauppauge, N.Y.) is placed in front of the lens to reduce unwanted reflection from the blue egg rollers 27. One of ordinary skill in the art could use different filters to reduce reflections from rollers of other color. In a preferred embodiment, an atmospheric pressure image is first collected and used as a reference image. Then a negative-pressure image is collected and compared to the reference image to detect a check or crack. There are two primary methods to capture a negative pressure image. The first is a shorter exposure time that is controlled by a digital pressure sensor 46, which is mounted on the side of vacuum chamber 23, and the pressure control block 47, which is housed in the control enclosure 41. The pressure control block 47 is programmable and triggers the camera 42 through an external trigger at a specified negative pressure of about 6.5 in. Hg. The second method is to use a long exposure time that begins with the start of the vacuum and ends slightly before the vacuum is released. This can typically be done with an internal camera trigger that can be software controlled. In most any embodiment, a computer 43, personal or single board, is used to capture, process, and save the images.

For a short exposure time method, a control circuit (FIG. 10) but housed in the control enclosure 41, enables the capturing of images of eggs while the eggs are subjected to a negative pressure gradient. Digital camera images are acquired at atmospheric and under negative pressure (FIGS. 11A and 11B) and stored on computer 43 (FIG. 1). The control circuit 4-9 (FIG. 10) has a normally-open push-button switch 44 connected to a Keyence CU-21TA control unit (Osaka, Japan) (not shown) and the air solenoid valve 19. Optionally, computer 43 can start the process instead of a physical button 44 in the control circuit (FIG. 10). One of ordinary skill in the art can readily determine which means for starting the process to use. When push-button 44 is pressed, computer 43 sends a software command to capture an atmospheric image via the internal camera trigger. Then the 120 volt, 4-way solenoid valve 19 is energized, which throws the compressed air ram, and creates a vacuum in the vacuum pump 12, which in turn pulls a vacuum in chamber 23 with lid 29. A digital pressure sensor 46, attached to the side of the egg chamber 23, continuously measures the pressure in chamber 23 with lid 29 and outputs a trigger signal to camera 42 when the set pressure is obtained. The trigger signal is output through a pressure control block 47 (Keyence AP-C40W Digital Pressure Sensor with a Keyence Ap-44 head). The set pressure, or trigger pressure, was experimentally determined to be approximately 6.5 inches of Hg but optimum pressure values can vary depending on the configuration of vacuum pump 12 and the size of chamber 23 with lid 29. The negative pressure continues to build until the timing circuit in the control unit (FIG. 10) switches the air solenoid 19 back to its original state. The pressure control block 47 records the minimum pressure which is always under 9 inches Hg. For testing purposes, an analog output of the pressure can be captured from the pressure control block, along with the camera intergration time from the control circuit (not shown), with an optional digital oscilloscope (FIG. 10) to ensure the negative image capture is completed before the negative pressure is released.

The software algorithm is common and basic to image processing. There are numerous different algorithms to detect checks or cracks from the enhanced images. For purposes of the present invention, one method will be described. After both the atmospheric pressure image (FIG. 11A) and the negative pressure image (FIG. 11B) are captured, the two images are processed by a real-time machine-vision algorithm. Image intensity changes, associated with the normal and negative atmospheric pressure images, are used to identify and isolate any checks and/or cracks. Since the egg cracks are open in the negative pressure image, the image intensity of the crack itself becomes much brighter relative to the image intensity of the check or crack at atmospheric pressure. Thus, any change detection algorithm, using frame difference or image ratio for example, is suitable to extract these intensity changes and to use them for online inspection.

Figure 11:
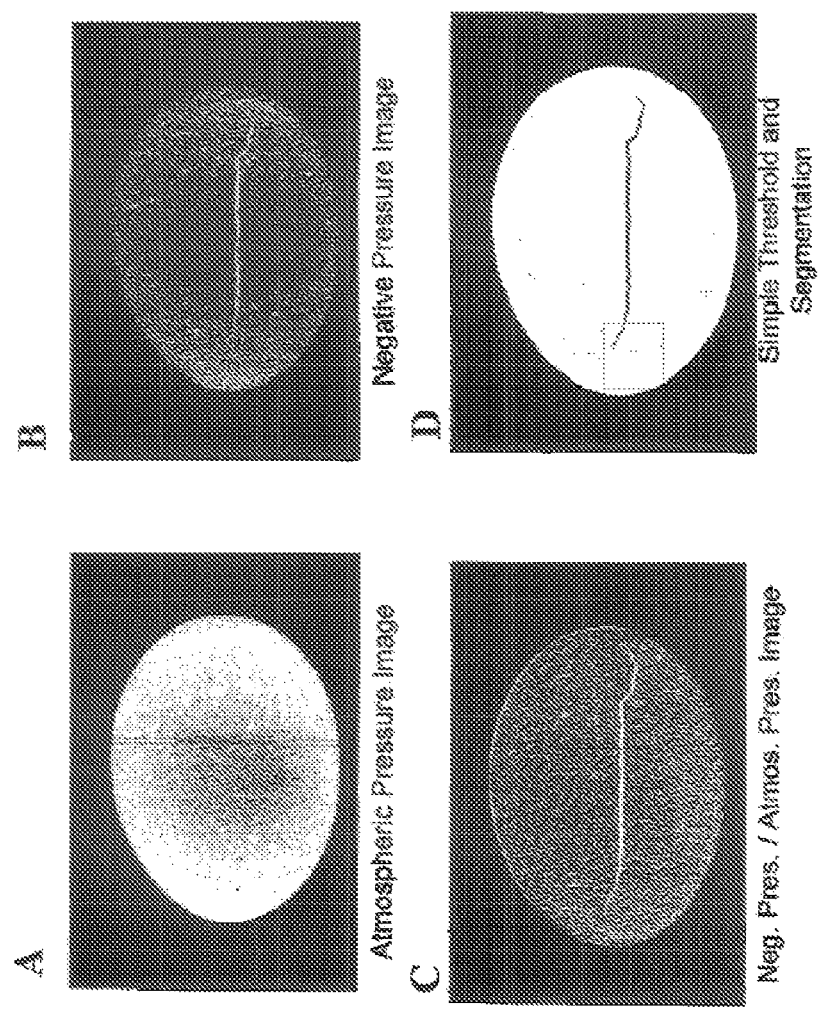
FIGS. 11A-11D are photographs showing images of an egg with a crack generated by imaging system 40.
Figure 12:
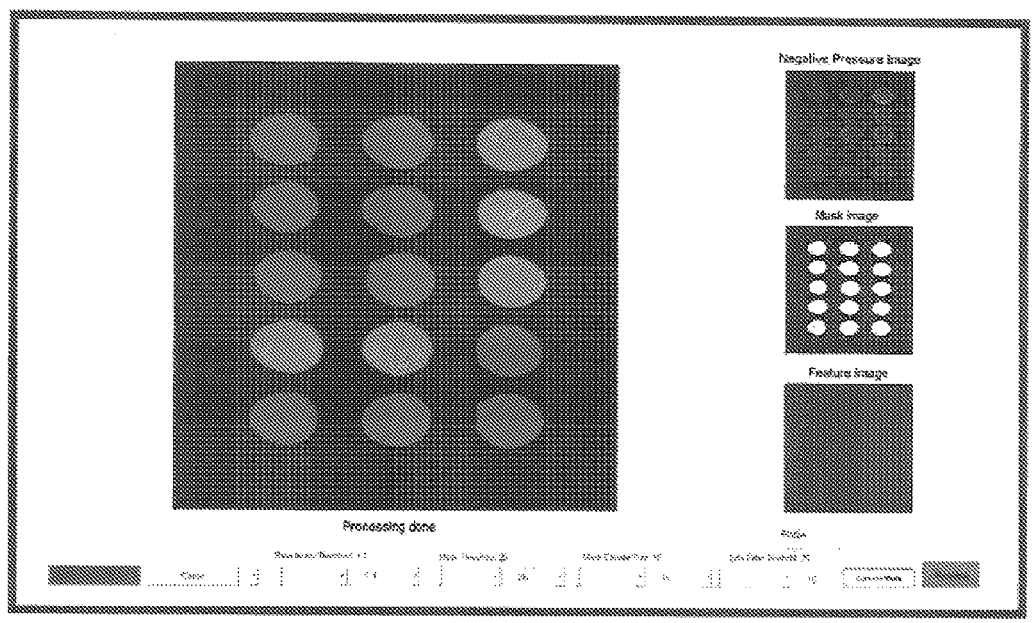
FIG. 12 is a photograph of images of 15 eggs as processed by the imaging system.

After comparing both frame-difference and image-ratio algorithms, an image ratio algorithm is further developed. The developed algorithm is summarized as follows. After obtaining a ratio image between the first image, the atmospheric pressure image, and the second image, the negative pressure image, a threshold is applied to the ratio image in order to remove features irrelevant to egg cracks. Most of the pixels with low ratio values are caused by random noise associated with camera 42 and are removed during threshold operation. A resulting binary image (FIG. 11C) is generated where pixels that have been identified as possible cracks are set to 1 and pixels that have not changed are set to 0 (zero). Thus, 0-value pixels indicate an intact eggshell. A 3×3 binary median filter is subsequently applied to the binary image in order to remove any remaining noise. In addition, a binary mask is generated for removing the background, i.e. non-egg features in the image. Potential check or crack features are then overlaid onto the egg mask, enabling a visual representation of each egg and any associated checks or cracks (FIG. 11D and FIG. 12). Optionally various morphological or segmentation filters can be applied to the results to further isolate the check(s) or crack(s) and remove false positives.

Another embodiment of the invention is to only capture the negative pressure image and use it with more sophisticated machine-vision algorithms to detect checks or cracks. The advantages of such a method would be that the eggs would never have to stop turning. Additionally, while rotating, rollers 27 could also pass across the field of view of camera 42 (translation) and images of the eggs collected as they both rotate and move through chamber 23, as would be the case in on-line processing, would be processed. Another embodiment of the present invention would be to use multiple cameras 42 to simultaneously image the whole surface of an egg or eggs in chamber 23.

For systems that process much fewer than about 15 eggs at a time, image system 40 is not needed (FIG. 13). Human inspectors can directly observe the eggs in the vacuum system with the lighting system to determine if a check or crack is present.

The foregoing detailed description is for the purpose of illustration. Such detail is solely for that purpose and those skilled in the art can make variations therein without departing from the spirit and scope of the invention.

LISTING OF ELEMENTS

10. Micro-Crack Detection System
11. Vacuum System
12. Vacuum Pump
13. Double Ended Air Cylinder
14. Six-inch PVC Cylinder
16. Gasket Sealed Aluminum Top
18. Gasket Sealed Aluminum Bottom
19. Solenoid Valve
21. Lights
22. Light Positioning Plate
23. Vacuum Egg Chamber
24. Constant Current Drivers
25. Potentiometers
26. Light-Aperture Plate
27. Egg Rollers
28. Light Guides
29. Chamber Lid
30. PVC Pipes
40. Image System
41. Control Enclosure
42. Camera
43. Computer
44. Push Button Switch
45. Control Unit
46. Digital Pressure Sensor

We claim:

1. A system that detects checks and/or cracks in avian eggs comprising: a vacuum system wherein said vacuum system includes a vacuum pump operatively connected to a control unit, the control unit operatively connected to a vacuum egg chamber, the vacuum egg chamber includes a lighting system located outside and under a vacuum box and the vacuum box wherein said lighting system includes lights operatively connected to a light-positioning plate and potentiometers, the light-positioning plate located outside and under said vacuum box, the potentiometers, light guides located inside said vacuum box and operatively connected to an aperture plate, the aperture plate located inside said vacuum box and operatively connected to said light guides, and a DC power supply operatively connected to said system that detects checks and/or cracks in avian eggs.

2. A system that detects checks and/or cracks in avian eggs comprising:
    a vacuum system wherein said vacuum system includes a vacuum pump operatively connected to a vacuum box, a control unit operatively connected to said vacuum system, and a vacuum egg chamber operatively connected to said vacuum pump and that includes lighting system operatively connected to said vacuum egg chamber, and the vacuum box wherein said vacuum box includes egg rollers operatively connected to said vacuum system, light guides located in said vacuum box, and a vacuum chamber lid.

3. A method for detecting checks and/or cracks in an avian egg comprising:
    a) placing at least one avian egg into a vacuum egg chamber,
    b) creating a negative pressure vacuum in said vacuum egg chamber,
    c) illuminating said at least one egg with a lighting system while under the negative pressure vacuum, and
    d) determining a presence of a crack and/or a check in said egg by taking an image using an imaging system.

4. The method of claim 3, wherein said negative pressure vacuum is created using a vacuum system wherein said vacuum system includes at least a vacuum pump operatively connected to a control box and the control box.

5. The method of claim 3 wherein said creating a negative pressure vacuum is accomplished rapidly to open an existing check and/or crack in an eggshell.

6. The method of claim 3 wherein said lighting system in the step of illuminating includes lights operatively connected to a light-positioning plate, the light-positioning plate operatively connected to said vacuum egg chamber, constant current drivers operatively connected to said lights, potentiometers operatively connected to said constant current drivers, light guides located inside said vacuum chamber and operatively connected to an aperture plate, and the aperture plate located inside said vacuum chamber and operatively connected to said light guides.

7. The method of claim 3 wherein an intensity of said lighting system can be adjusted for individual or multiple eggs.

8. The method of claim 3 wherein said imaging system includes at least one camera, a computer, and a pressure control box.

9. The method of claim 3 wherein said step of determining the presence of a check and/or crack in said egg is performed with images taken at negative pressure and at atmospheric pressure.

10. The method of claim 3 wherein said placing of at least one avian egg can be accomplished with an automatic on-line system.

* * * * *